(12) United States Patent
Morris et al.

(10) Patent No.: US 9,619,678 B2
(45) Date of Patent: Apr. 11, 2017

(54) RFID INTERROGATION PROBE

(71) Applicant: CRYOGATT SYSTEMS LIMITED, Buxted (GB)

(72) Inventors: Geoffrey Morris, Pinner (GB); James Douglas, Kings Langley (GB)

(73) Assignee: Cryogatt Systems Limited, Buxted Sussex (GB)

( * ) Notice: Subject to any disclaimer, the term of this patent is extended or adjusted under 35 U.S.C. 154(b) by 0 days.

(21) Appl. No.: 14/411,225

(22) PCT Filed: Jul. 11, 2013

(86) PCT No.: PCT/GB2013/051839
§ 371 (c)(1),
(2) Date: Dec. 24, 2014

(87) PCT Pub. No.: WO2014/009729
PCT Pub. Date: Jan. 16, 2014

(65) Prior Publication Data
US 2015/0205986 A1 Jul. 23, 2015

(30) Foreign Application Priority Data

Jul. 11, 2012 (GB) .................... 1212415.2

(51) Int. Cl.
  *G06K 7/00* (2006.01)
  *G06K 7/10* (2006.01)
  *B01L 3/00* (2006.01)
  *G06K 19/04* (2006.01)
  *G06K 19/077* (2006.01)
  (Continued)

(52) U.S. Cl.
  CPC ....... *G06K 7/10336* (2013.01); *A01N 1/0236* (2013.01); *A01N 1/0257* (2013.01); *A01N 1/0268* (2013.01); *A61J 1/18* (2013.01); *B01L 3/545* (2013.01); *G06K 7/0008* (2013.01); *G06K 19/04* (2013.01); *G06K 19/07749* (2013.01); *G06K 19/07762* (2013.01); *H01Q 1/2216* (2013.01); *H01Q 7/00* (2013.01);
  (Continued)

(58) Field of Classification Search
  CPC .......... G06K 17/0022; G06K 17/0025; G06K 17/0045; G06K 17/0051; G06K 19/0723
  USPC ....... 235/439, 462, 462.46, 472.02
  See application file for complete search history.

(56) References Cited

U.S. PATENT DOCUMENTS 6,222,450 B1  4/2001 Clements
6,595,418 B1  7/2003 Igarashi et al.
(Continued)

FOREIGN PATENT DOCUMENTS

CN   202084068 U   12/2011
DE   42 11 545 C1   8/1993
(Continued)

OTHER PUBLICATIONS

IV Witness document, Research Instruments Ltd. (Applicant became aware off this document in 2004).
(Continued)

*Primary Examiner* — Daniel St Cyr
(74) *Attorney, Agent, or Firm* — Kilpatrick Townsend & Stockton LLP

(57) ABSTRACT

An RFID interrogation probe (1) comprises a ring shaped housing (2), having a maximum thickness (I) (measured along its cylindrical axis) which is less than the innermost diameter (di) of the housing, and a looped antenna (3) housed within the ring shaped housing.

9 Claims, 6 Drawing Sheets

(51) Int. Cl.
*H01Q 1/22* (2006.01)
*H01Q 7/00* (2006.01)
*A01N 1/02* (2006.01)
*A61J 1/18* (2006.01)
*G01N 1/42* (2006.01)
*G01N 35/00* (2006.01)

(52) U.S. Cl.
CPC .... *A61J 2205/60* (2013.01); *B01L 2300/1894* (2013.01); *G01N 1/42* (2013.01); *G01N 2035/00782* (2013.01)

(56) References Cited

U.S. PATENT DOCUMENTS

| | | | |
|---|---|---|---|
| 7,350,703 | B2 | 4/2008 | Ambartsoumian |
| 2003/0001739 | A1 | 1/2003 | Clucas et al. |
| 2005/0134460 | A1 | 6/2005 | Usami |
| 2005/0231330 | A1 | 10/2005 | Drews et al. |
| 2005/0247782 | A1 | 11/2005 | Ambartsoumian |
| 2009/0188675 | A1 | 7/2009 | Bloom et al. |
| 2010/0066373 | A1 | 3/2010 | Arnold et al. |
| 2010/0270381 | A1 | 10/2010 | Baba et al. |
| 2010/0302040 | A1 | 12/2010 | Davidowitz et al. |
| 2010/0328037 | A1 | 12/2010 | Thomas et al. |
| 2011/0199187 | A1 | 8/2011 | Davidowitz |

FOREIGN PATENT DOCUMENTS

| | | |
|---|---|---|
| DE | 198 24 643 A1 | 11/1999 |
| DE | 199 57 647 A1 | 6/2001 |
| DE | 101 50 458 A1 | 4/2003 |
| EP | 1 324 255 A2 | 7/2003 |
| EP | 2 315 163 A1 | 4/2011 |
| GB | 2 450 531 A | 12/2008 |
| JP | 2007-208646 A | 8/2007 |
| WO | 2005/109332 A1 | 11/2005 |
| WO | 2005/115621 A1 | 12/2005 |
| WO | 2009/004366 A1 | 1/2009 |

OTHER PUBLICATIONS

The International Search Report corresponding to the PCT/GB2013/051839 application filed Jul. 11, 2013.

RFID INTERROGATION PROBE

CROSS-REFERENCE TO RELATED APPLICATIONS

This application is a U.S. National Stage of PCT Application No. PCT/GB2013/051839, filed Jul. 11, 2013, which claims priority to Foreign Application No. 1212415.2 GB, filed Jul. 11, 2012, the entire contents of each of which are incorporated herein by reference in their entirety for all purposes.

TECHNICAL FIELD

The present invention relates to an RFID probe, particularly to an RFID probe for reading disposable containers for cryogenic storage.

BACKGROUND

Biological samples may be preserved by cryogenic freezing. The biological samples are usually stored in disposable containers (disposables). The shape of the disposable container used depends on the type of sample. Examples of commonly used disposable containers include vials, straws and bags. The disposable container is stored at low temperatures in a Dewar flask typically filled with liquid nitrogen at a temperature of −196° C.

Where samples are stored in straws, a plurality of straws are usually kept in a visotube, a plurality of visotubes are in turn typically kept in a goblet, and a plurality of goblets are typically kept in a canister which is stored in the Dewar.

Stored biological samples can be identified by writing on the disposable containers themselves, or by labels stuck to the containers. These labels may be handwritten or printed and can include bar codes. However, such methods of identification have associated disadvantages; written notes on containers can easily be erased or smudged and labels containing handwritten notes and printed text or barcode information can fall off the disposable containers while they are stored inside the Dewar leading to unidentifiable samples. These problems are exacerbated by the cold conditions in which biological samples must be kept.

When performing an audit of biological samples stored in cold storage (at temperatures of −196° C.), the samples should not be allowed to warm up to a temperature greater than −130° C. It is therefore desirable to minimise the amount of time spent outside of the Dewar wherever possible.

Recording, monitoring and auditing of samples in cold storage takes a considerable amount of time and effort, even when samples are labelled using barcodes. An additional and undesirable increase in the time taken to record or audit samples arises as a result of frost which forms on the surfaces of disposable containers and their labels when they are removed from liquid nitrogen into relatively warmer temperatures. It is common for samples to be stored for many years (e.g. 15 years) but even after just one year in storage, the layer of frost which builds up on a disposable container can make it impossible to make an optical reading of a bar code on a label using a bar code reader because a layer of frost blocks or diffracts the light of the bar code reader. The container cannot be warmed up to remove frost as this would lead to destruction of the sample. The frost can be wiped off the disposable container but this contributes to an undesirable increase in the amount of time taken to read the sample.

It is known that Radio Frequency ID (RFID) tags can be used to monitor a plurality of disposable containers stored at low temperatures of down to −196° C. An RFID reader can be used to write information to and read information from the RFID tag before, after, or during cryogenic storage.

An RFID tag includes an RF transmitter and an RF receiver. An RFID reader can be used to transmit an encoded radio signal to a tag to interrogate it. Upon receiving the interrogation signal, the RFID tag transmits its identification information to the reader. This identification information may be a unique serial number assigned to a particular patient or to a particular sample.

In Europe and other countries outside of the US, RFID components for medical storage operate at an approved frequency of 13.56 MHz. It is important that the frequency used for the RFID tag does not lead to any undesirable interference with other electronic medical equipment. Lower medically approved frequency bands such as 125 KHz do not provide enough signal bandwidth to provide the tag with a useful user defined memory.

EP2315163 discloses an elongate annular antenna for transmitting and receiving radio frequency signals. The antenna also includes screening or shielding means which add to the undesirable bulk of the antenna.

STATEMENT OF INVENTION

Accordingly, the present invention aims to solve the above problems by providing, according to a first aspect, a sleeve according to claim 1.

Ring shaped housing should be understood to mean a housing with a hole which extends through the housing from a first end to a second end. The housing has a cylindrical axis which extends along the length of the hole from an upper side of the housing to a lower side of the housing.

Preferably, the ring shaped housing defines a hole capable of receiving a cryogenic canister so that when the canister is located within the hole, the looped antenna of the RFID probe encircles the cryogenic canister to read or write to RFID tags located on and/or inside of the canister. For example, the RFID tags may be located on a goblet and/or a straw which is placed inside the cryogenic canister. The RFID probe would also be capable of encircling an individual RFID goblet and/or an RFID straw.

The hole of the ring shaped housing enables the RFID probe to be positioned around a cryogenic canister and scanned along the entire length of the canister.

When viewed as a cross section transverse to the cylindrical axis, the housing has an inner perimeter which defines the shape of the hole and an outer perimeter which defines the shape of the outer walls of the housing. The inner perimeter may be circular but can also be another shape such as an oval or a polygon. Similarly, the outer perimeter of the housing may be circular or substantially circular but may also take another shape, for example the outer perimeter could be rectangular. The inner perimeter and outer perimeter may be the same or substantially the same shape as each other, for example they may both be circular. Alternatively, the inner and outer perimeter may differ in shape. For example, the inner perimeter may be circular but the outer perimeter may be rectangular.

It should be understood that irrespective of whether or not the inner perimeter is circular, the cylindrical axis of the housing is the central axis running through the housing, from an upper side to a lower side of the housing.

The innermost diameter of the ring shaped housing is measured transverse to the cylindrical axis.

It should also be understood that where the inner perimeter of the ring shaped housing has any shape other than circular, the innermost diameter is the maximum measurement possible from one point on the inner perimeter to the opposite side of the inner perimeter along a plane transverse to the cylindrical axis. For example, if the inner perimeter was a square, the innermost diameter would be the length of the diagonal of the square.

The RFID probe is versatile and easily manoeuvrable due to its small length along the cylindrical axis relative to the innermost diameter of the housing.

Preferably, the maximum length of the ring shaped housing along its cylindrical axis is less than ¾ of the length of the innermost diameter of the ring shaped housing.

Even more preferably, the maximum length of the ring shaped housing along its cylindrical axis is less than ⅔ of the length of the innermost diameter of the ring shaped housing.

Even more preferably, the maximum length of the ring shaped housing along its cylindrical axis is less than ½ of the length of the innermost diameter of the ring shaped housing.

Preferably, the innermost diameter of the ring shaped housing is no less than 70 mm.

Even more preferably, the innermost diameter of the ring shaped housing is no less than 80 mm.

Preferably, the looped antenna includes no more than 2 loops

Preferably, the ring shaped housing further comprises connection means for connecting the housing to a support.

In this way the RFID probe can easily be mounted to different types of support thereby providing a versatile tool for both reading and writing to RFID tags.

The support may be a stand. Alternatively, the support may be a rod.

Where the support stand is a rod, the RFID probe and the rod form a "wand" which is suitable for lowering into a Dewar to encircle a canister and therefore to read RFID tags placed on any of the: canister; goblet; straw; and visotube ID's for example during an audit of samples.

When the support is a support stand (i.e. "legs" upon which the RFID probe can stand), the RFID probe may be used to allocate RFID identification to a straw as soon as it is filled with biological material in the laboratory. At this point it may also be used to provide RFID identification to a visotube containing a number of straws (a computer system operated by the user can be used to record that a given number of straws, each with their unique ID, are placed in a given visotube with its own unique ID). This could also typically be extended to write a unique ID to a goblet and to associate the goblet with the visotubes that it contains.

Alternatively, the RFID probe could also be mounted directly to a cryogenic flask/Dewar using a suitable mechanical fixing i.e. the support can be the flask/Dewar itself. For example, the RFID probe could be mounted at the mouth of a cryogenic flask used for transportation of samples in order to read and/or write to straws, visotubes etc. placed in the cryogenic flask for temporary storage.

The connection means is preferably a fixing hole in the ring shaped housing.

Optionally, the connection means is two fixing holes and the ring shaped housing defines a cavity for electrical components, the cavity being located in-between the two fixing holes.

Optionally, the RFID probe is provided in combination with a support stand.

Optionally, the RFID probe is provided in combination with a rod.

Optionally, the RFID probe is provided in combination with an RFID reader module wherein the antenna of the RFID probe is communicably connected to the RFID reader module.

The present invention will now be disclosed by way of example only, with reference to the accompanying figures, in which:

FIG. 1a is a plan view of an RFID probe according to the present invention and FIG. 1b shows a cross section of the RFID probe along line A-A as shown in FIG. 1a;

DESCRIPTION

Figure 1A:
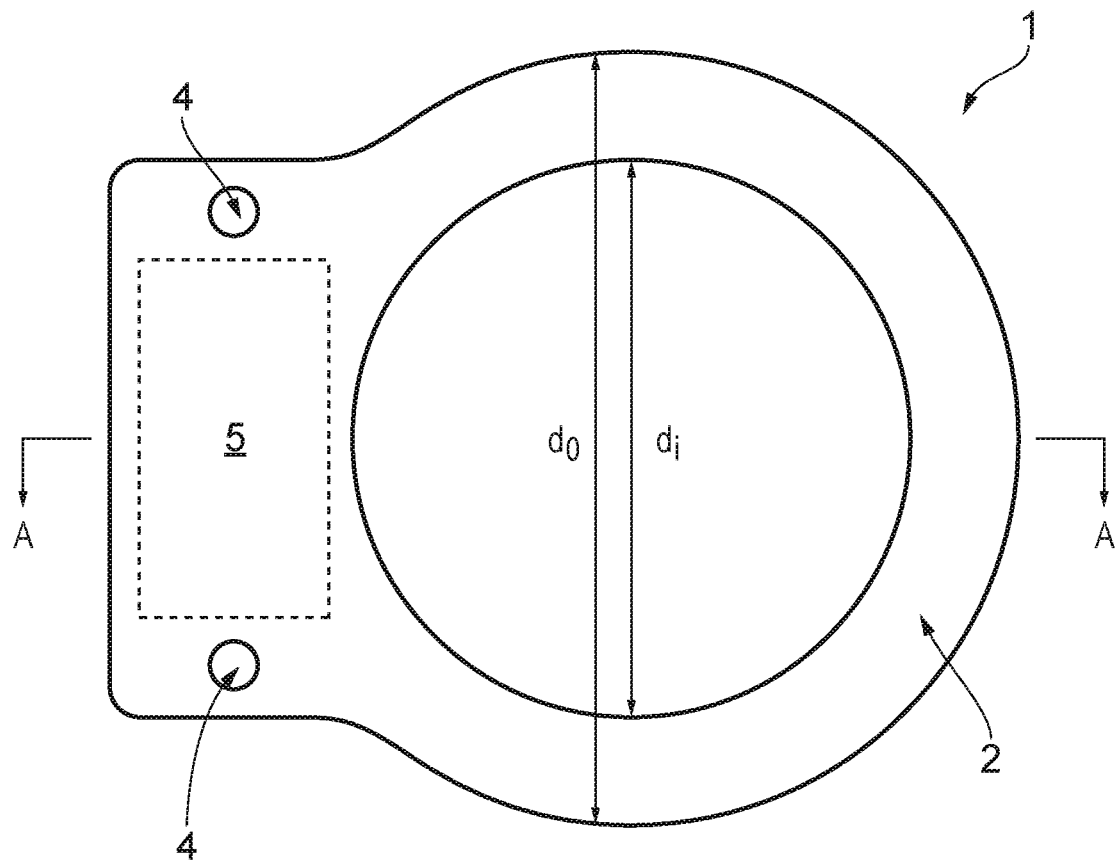
Figure 1B:
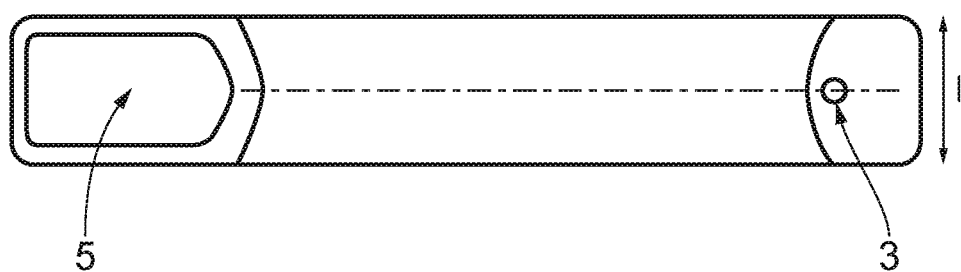

FIGS. 1a and 1b show an RFID probe 1 having a ring shaped housing 2 which houses a looped antenna (not shown). The length of the ring shaped housing 1 along its cylindrical axis is less than the outermost diameter $d_o$ of the housing. The length of the ring shaped housing 1 is also less than the innermost diameter $d_i$ of the housing.

The ring shaped housing 2 includes connection means 4 in the form of fixing holes. The fixing holes are bored holes which extend from one side of the housing to the other.

The ring shaped housing 2 also includes a cavity 5 which can be used to house electronics such as "matching" circuitry that matches the looped antenna to a coaxial cable and therefore to an RFID reader that is at the far end of the coaxial cable. In this way, the design enables the RFID probe to be placed into a cold environment (such as a Dewar or a "transport flask" filled with liquid nitrogen) whilst keeping the reader electronics outside of the cold environment (e.g. wand lowered into Dewar, or at the mouth of a small "transport flask" containing liquid nitrogen).

Alternatively, a complete RFID reader could be housed in the cavity. Such a design would be particularly useful where the RFID probe is to be used in temperatures of around −40° C. and above.

Figure 2:
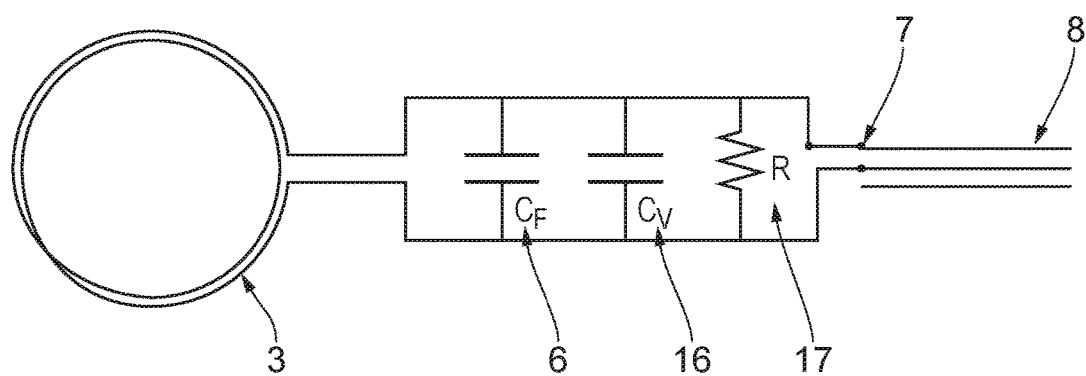
FIG. 2 is a schematic diagram of the looped antenna and connecting circuitry of the RFID probe.

The looped antenna 3 of the RFID probe 1 is shown in more detail in FIG. 2.

In the embodiment shown in FIG. 2, the antenna coil of the looped antenna has 2 turns. The diameter of looped antenna is 80 mm and the copper wire used to form the antenna has a 0.75 mm diameter giving an antenna coil inductance of about 2 μH.

The looped antenna 3 is connected to a coaxial cable 8 via a "matching circuit" and a coaxial connector 7. The "matching circuit" is made up of: a fixed capacitor ($C_F$) 6, a variable capacitor ($C_V$) 16 and a resistor (R) 17 all connected to each other in parallel.

In the embodiment shown in FIG. 2, the resistor R has a fixed value of 60 ohms, the fixed value capacitor ($C_F$) 6 has a value of around 150 pf (picofarads) and the variable capacitor $C_V$ is variable over a range of 10 pf to 50 pf so that it can be set to "match" the RFID probe antenna to the coaxial cable 8 and therefore to an RFID reader module located at the far end of coaxial cable 8.

The function of the resistor 17 is to form part of the matching circuitry but also to provide the required circuit bandwidth ("Q factor") in order to allow the standard RFID transmit and receive data bandwidth to propagate through to the looped antenna.

The parameters described above are those which have been chosen to optimise antenna performance for an antenna 3 having only 2 coils.

The antenna may be made up of any number of coils, for example up to 10 coils, in which case different values of the fixed capacitor 6, variable capacitor 16 and fixed resistor 17 would be chosen in order to optimise antenna performance for the given number of coils.

Figure 3A:
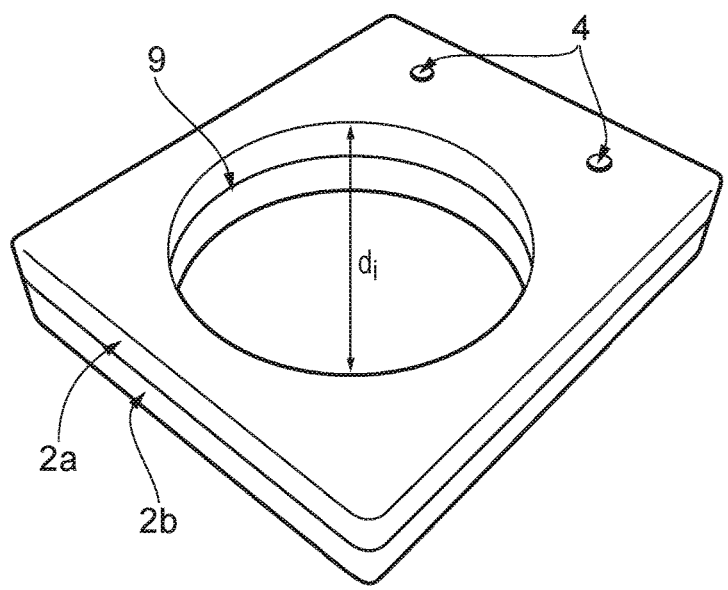
FIG. 3 is a picture of the ring shaped housing of the probe, the ring shaped housing having two halves.
Figure 3B:
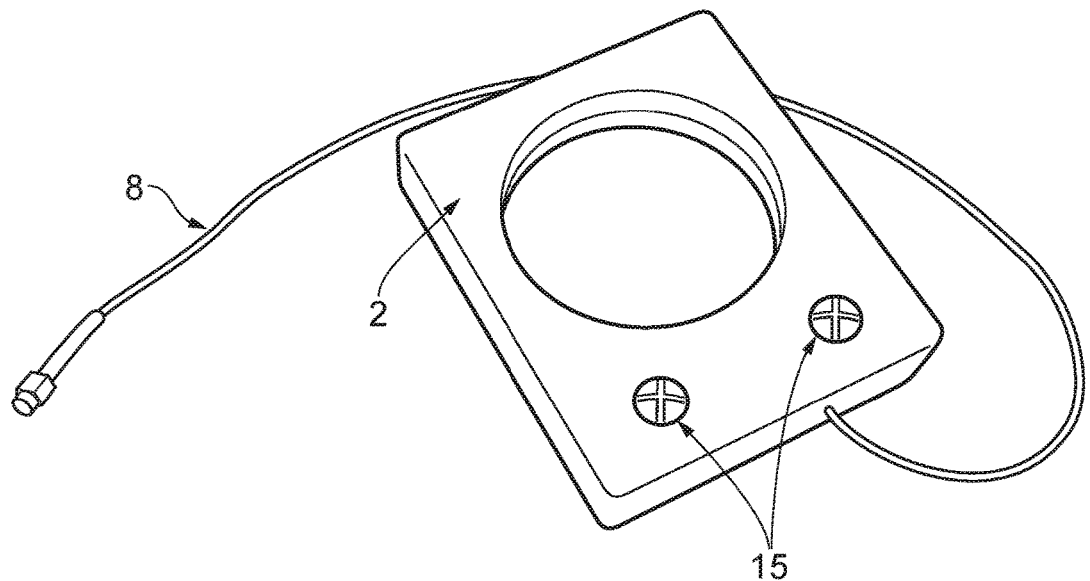
Figure 4:
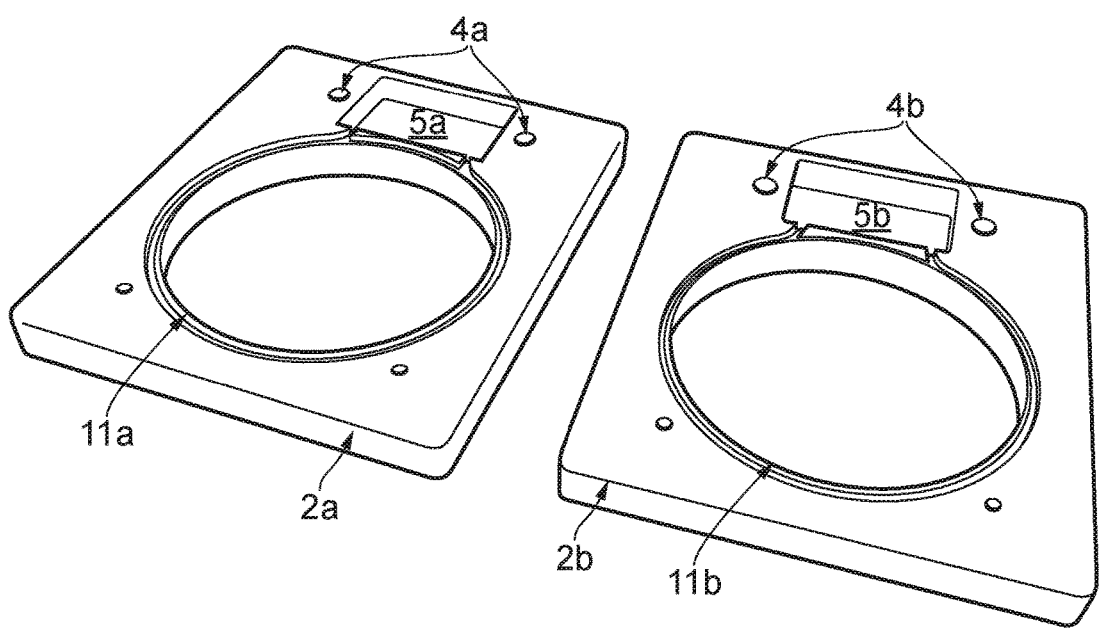
FIG. 4 is a picture of the housing of FIG. 3 with the two halves separated.

FIGS. 3a, 3b and 4 show a ring shaped housing 2 formed of two halves 2a, 2b. FIGS. 3a and 3b show the two halves in an assembled configuration.

As shown in FIG. 3a, the first half of the housing 2a is placed on top of the second half of the housing 2b to form a hermetically sealed interface 9. The hermetically sealed interface can be achieved by a "welding" type adhesive.

Fixing means 15 such as nuts and bolts inserted into fixing holes 4a, 4b also act to hold the two halves 2a 2b of the ring shaped housing together.

Each half 2a, 2b of the ring shaped housing 2 has a circular inner profile and a rectangular outer profile.

FIG. 4 shows the two halves 2a and 2b of the ring shaped housing in an unassembled configuration.

Each half includes connection means in the form of two fixing holes 4a, 4b bored through the housing 2a, 2b. In addition, each half of the housing defines a cavity half 5a, 5b. The cavity halves 5a, 5b match up to form the cavity 5 when the two halves of the housing are assembled together. The fixing holes 4a, 4b of each half are located either side of cavity halves 5a and 5b.

Each half of the housing 2a, 2b also includes a track 11a, 11b to receive the looped antenna. The track enables the two halves 2a, 2b to be assembled around the looped antenna 3 to create a seal.

Figure 5:
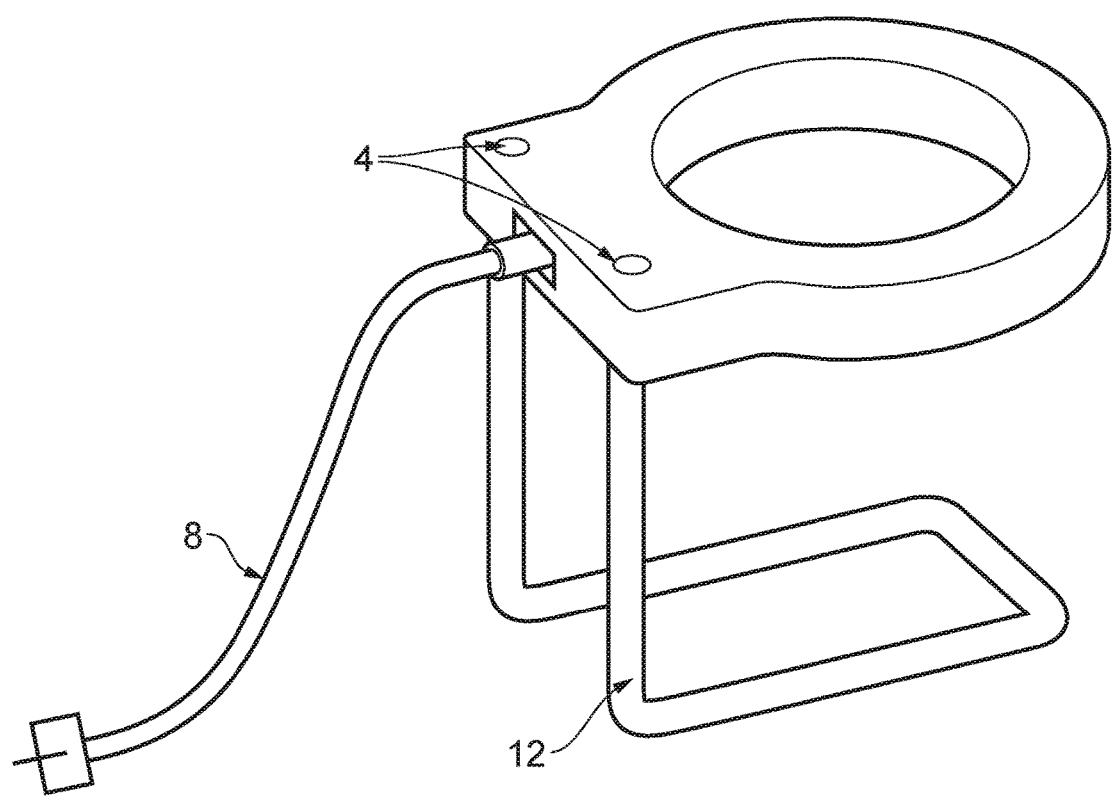
FIG. 5 is a perspective view of the RFID probe in combination with a stand.

FIG. 5 shows the RFID probe 1 mounted on a stand 12. The stand is L-shaped and is attached to the RFID probe 1 at connection means 4 using fixing means such as screws or bolts. When mounted on a stand 12, the RFID probe can be mounted on a surface such as a laboratory bench. This arrangement is particularly useful when the probe is used to write (i.e. to program) RFID tagged disposable containers.

Figure 6:
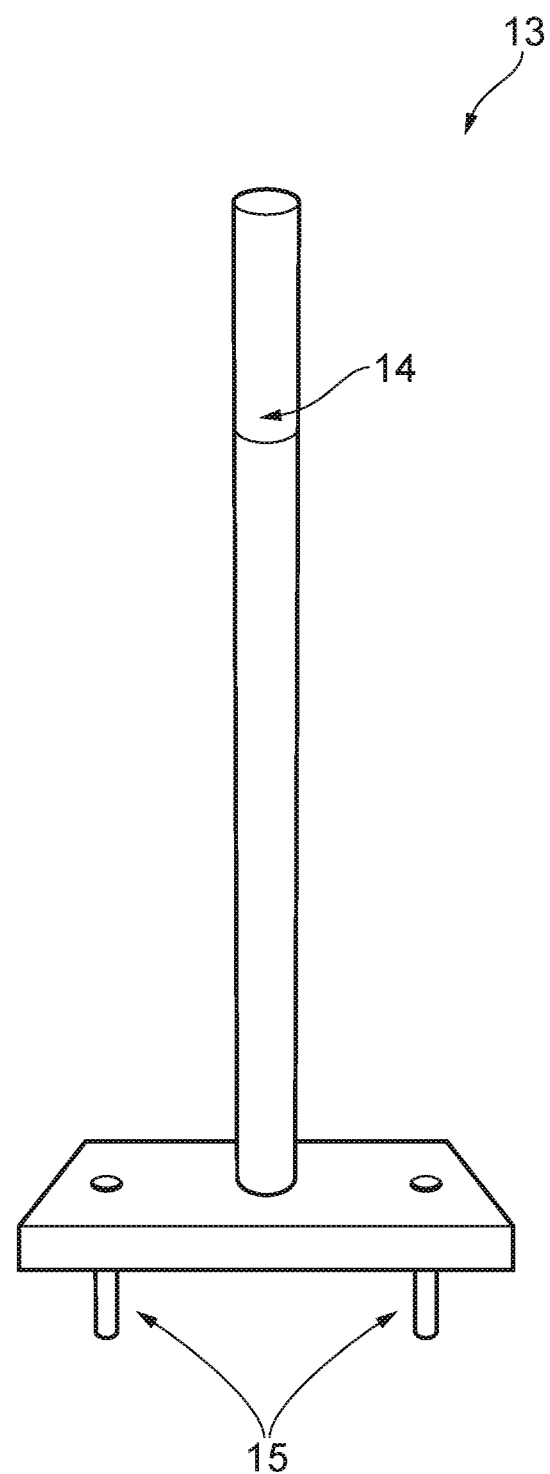
FIG. 6 is a picture of a rod for attachment to the RFID probe.

FIG. 6 shows a rod 13 on which the RFID probe 1 can be mounted. fixing means 15 such as screws or bolts can be used to fasten the rod to the RFID probe. In this arrangement, the rod 13 can be used to lower the RFID probe into a Dewar so that RFID tagged containers can be read whilst inside the Dewar. The rod 13 includes a handle 14.

The rod 13 and/or the handle 14 may be made of a thermally insulating material to avoid undesirable heat transfer between the rod and the Dewar.

The RF coaxial cable can be simply plugged into an RF port standard RFID reader, that is, a port for transmitting and receiving the 13.56 MHz "carrier" frequency. The RFID reader can then be connected to a processor/PC.

The RFID probe of the present invention can be used in the writing of RFID tags and/or the reading of RFID tags by sending appropriate signals to the looped antenna 3.

Assuming that the transmitted power of the reader electronics is chosen appropriately, the small maximum length along the cylindrical axis relative to the innermost diameter of the antenna coils enables any unwanted exciting (transmitted) field outside the probe to be kept low whilst the field inside the hole of the probe is high enough to activate RFID tags. In this way, the need for extra shielding of the antenna is minimised.

The foregoing description of the preferred embodiments of the invention have been presented for purposes of illustration and description, it is not intended to be exhaustive or to limit the invention to the precise form disclosed, and modifications and variations are possible in light of the above teachings.

It is intended that the scope of the invention be defined by the claims appended hereto.

The invention claimed is:

1. A radio frequency identification (RFID) interrogation probe for interrogating RFID tagged disposable cryogenic storage containers comprising:
   a ring shaped housing having a length from an upper side of the housing to a lower side of the housing which is less than an innermost diameter of the ring shaped housing, the length being in an axial direction, the ring shaped housing defining an orifice adapted to encircle one or more RFID tagged cryogenic containers, and the ring shaped housing further comprising support legs mounted to the ring shaped housing;
   a looped antenna housed within the ring shaped housing; and
   an RFID reader module housed within the ring shaped housing, the RFID reader module communicably connected to the antenna for transmitting an encoded radio signal to the RFID tagged cryogenic container.

2. The RFID interrogation probe of claim 1, wherein an innermost diameter of the ring shaped housing is no less than 70 mm.

3. The RFID interrogation probe of claim 1, wherein the looped antenna includes no more than 2 loops.

4. The RFID interrogation probe of claim 1 wherein the ring shaped housing further comprises a connection component that connects the housing to a support.

5. The RFID interrogation probe of claim 4, wherein the support includes a stand or a rod.

6. The RFID interrogation probe of claim 5, wherein the connection component includes two fixing holes and wherein the ring shaped housing defines a cavity for electrical components, the cavity being located in-between the two fixing holes.

7. The RFID interrogation probe of claim 1, wherein an inner perimeter of the ring housing is circular in cross section.

8. A radio frequency identification (RFID) interrogation probe for interrogating RFID tagged disposable cryogenic storage containers comprising:
   a ring shaped housing having a length from an upper side of the housing to a lower side of the housing which is less than an innermost diameter of the ring shaped housing;
   a looped antenna housed within the ring shaped housing; and
   an RFID reader module communicably connected to the antenna for transmitting an encoded radio signal to the RFID tagged container,
   wherein the ring shaped housing further comprises a connection component that connects the housing to support legs, and wherein the ring shaped housing defines a cavity for electrical components, and wherein:
      the RFID reader module is located inside the cavity of the ring shaped housing; and
      the RFID interrogation probe further comprises matching circuitry housed within the cavity that matches the looped antenna to the RFID reader module.

9. The RFID interrogation probe of claim 8, wherein the matching circuitry comprises:

a fixed capacitor, a variable capacitor, and a resistor all connected to each other in parallel.

* * * * *